United States Patent [19]
Rountree et al.

[11] 3,972,226
[45] Aug. 3, 1976

[54] SLIT IMPACT AIR SAMPLER

[76] Inventors: Calvin Briggs Rountree, 9028 Gatewood Drive, Jonesboro, Ga. 30236; Donovan Charles Philpin Mitchell, 1511 Yale Drive, Hollywood Hills, Fla. 33021

[22] Filed: Aug. 12, 1975

[21] Appl. No.: 604,004

[52] U.S. Cl. .................................................. 73/28
[51] Int. Cl.² ............................................ G01N 15/00
[58] Field of Search ......................................... 73/28

[56] References Cited
UNITED STATES PATENTS

| | | | |
|---|---|---|---|
| 2,310,871 | 2/1943 | Robertson | 73/28 |
| 2,312,295 | 2/1943 | Dahlman et al. | 73/28 |
| 3,475,951 | 11/1969 | Goetz | 73/28 |

Primary Examiner—S. Clement Swisher
Attorney, Agent, or Firm—Harold L. Marquis

[57] ABSTRACT

A slit impact air sampler for collecting viable organisms in air borne particles at a controlled rate. The rotating platform upon which a collecting plate is positioned can be rotated at ten different speeds through a variable speed transmission. The height of the slit above the collecting plate can be adjusted while maintaining the slit in a radial position to the plate.

7 Claims, 5 Drawing Figures

SLIT IMPACT AIR SAMPLER

DESCRIPTION OF THE PRIOR ART

A number of different types of instruments have been developed to measure biological contamination of the air. One of the more successful types has been the slit impact air sampler. It consists of an air tight chamber enclosing a platform upon which a collecting plate is positioned. Air is drawn at a controlled rate through a narrow inlet slit in the top of the sampler. Particles in the air stream are impacted upon the collecting plate located beneath the slit. The collecting plate may have a dry or coated surface, or contain a suitable medium, such as agar. The air leaves the chamber through an opening in the base or sidewall. A vacuum source is attached to the opening to draw a constant flow of air through the sampler.

The quantity and types of viable organisms in air borne particles can be determined by standard bacteriological methods. For example, where the viable particles are deposited on an agar surface, the bacterial colonies can be incubated in the medium and can be counted and identified under a microscope.

In order to secure a uniform particle distribution on the solid surface, the platform is rotated at a uniform rate by an electric motor or clock mechanism in some samplers, such as the Fort Detrick Slit Sampler, as described in "Sampling Microbiological Aerosols," Public Health Monograph No. 60, at 36. The slit tube in this sampler is threaded into the top of the sampler and may be adjusted to the desired height above the collecting plate by turning the tube up or down; the height desired depends upon the concentration of particles in the air, the air flow rate and the type of particles to be collected.

The Casella Slit Sampler (Pub. Health Mono. No. 60, at 38) has a gear changing mechanism so that the rotating platform can be rotated at three different speeds.

It is desirable to be able to rotate the platform at different rotation speeds in order to achieve optimum uniformity in the distribution of particles on the collecting plate. The plate is rotated rapidly if there is a high concentration of microbes in the air so that the microbe colonies do not pile on top of each other, which makes an accurate count after incubation difficult. If the concentration is low, the plate is rotated slowly to allow sampling a large quantity of air and insure the validity of the low count.

Even greater uniformity in particle distribution could be achieved if more than three rotation speeds were available to permit the operator to select the speed most suitable for the sampling conditions.

Because the medium in the collecting plate often varies in depth, it is desirable to be able to adjust the height of the slit above the medium in the collecting plate. While the slit height on some samplers, such as the Fort Detrick Sampler, is adjustable, the slit is rotated in the adjustment process so that it is in the desired radial position to the collecting plate only in steps of 180°. The greatest uniformity in particle distribution on the collecting plate is achieved when the slit is in the radial position. Samplers in which the height can only be adjusted in steps of 180° do not permit the infinite height adjustments desirable for different conditions.

OBJECTS OF THE PRESENT INVENTION

The principal object of the present invention is to develop a sampler with more than three rotation speeds for the collecting plate. A second object is to develop a sampler in which the slit tube can be raised or lowered with the slit always remaining in the same radial position to the collecting plate.

BRIEF DESCRIPTION OF THE DRAWINGS

Referring to FIG. 1, the air sampler includes a lower base 1 and impact chamber 2, which are attached together by spring clamps 3 or otherwise to permit easy removal of the impact chamber 2. The impact chamber 2 and lower base 1 may be hermetically sealed together. Located in the impact chamber 2 is a rotating platform 4 mounted on an output shaft 5 turned by a power source in the lower base 1.

A slit tube assembly 6 projects through the upper wall 7 of the impact chamber 2 so that the axis of the slit tube is located approximately midway between the center and periphery of the rotating platform 4.

Figure 1:
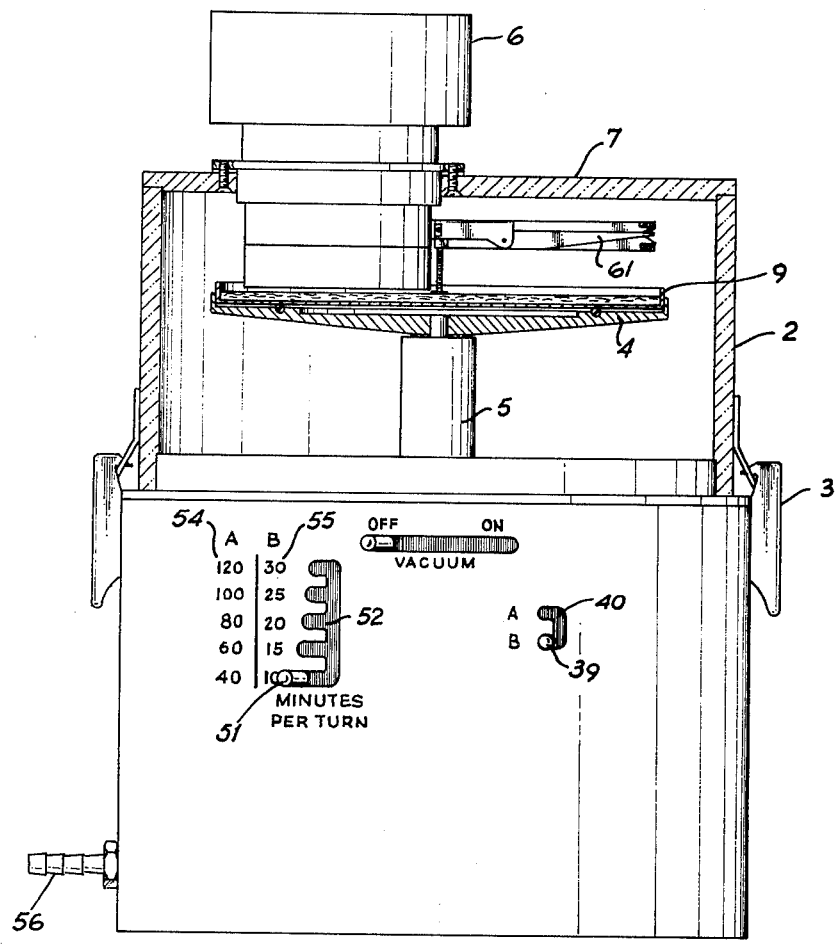
FIG. 1 is a front elevation of the slit impact air sampler.
Figure 3:
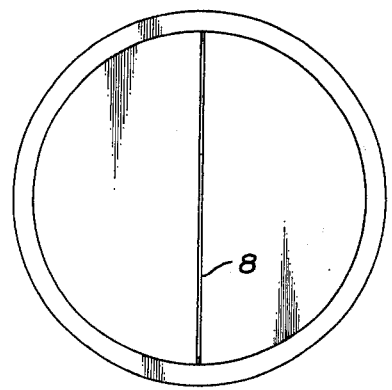
FIG. 3 is a bottom view of the slit tube.

Air enters through the slit 8, as shown in FIG. 3, impacting particles upon a collecting plate 9, as shown in FIG. 1, located on the rotating platform 4 immediately below the slit. The collecting plate may have a dry or coated surface, or contain a suitable gelatinous medium such as a layer of agar or gelatin. An outlet passage 56 is connected to the impact chamber 2 through an opening (not shown) in the base of the impact chamber 2. A vacuum pump is attached to the outlet passage 56 to insure an adequate and uniform flow of air through slit 8, impacting particles into the collecting plate 9.

Figure 2:
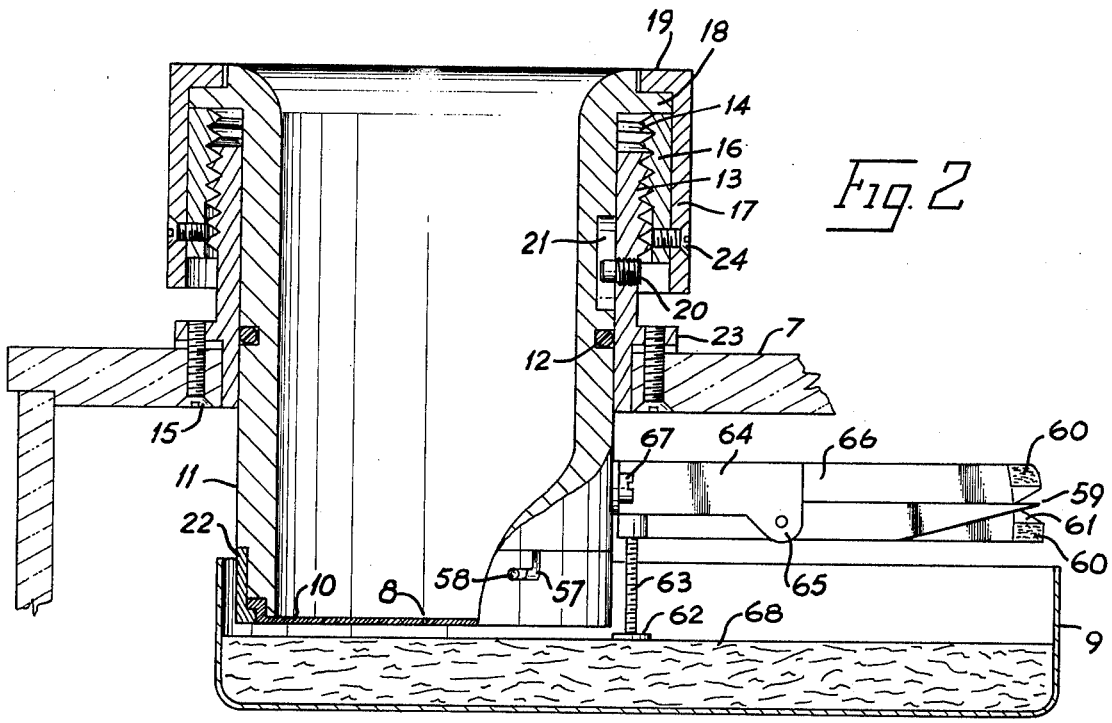
FIG. 2 is a cross-section of the slit tube taken along the vertical plane through the tube. A gap or height indicator is also shown in FIG. 2.

The construction of the slit tube assembly 6 is shown in detail in FIG. 2. A slit plate 10 with a narrow slit 8 traversing the diameter of the plate is removably attached by a ring 22 or otherwise to the bottom of the inner tube 11. The ring 22 has one or more L shaped slots 57 in its side wall, each of which fit over a pin 58 projecting from the inner tube 11. In this way the ring 22 can be held secure but easily removed by simply twisting and pulling down. The slit plate 10 can be easily replaced by a slit plate with a slit of a different width to achieve the desired air flow. The inner tube 11 may have a seal 12 encircling its outer surface to produce an air tight seal between the inner tube 11 and the outer sleeve 13, which is fitted around it. A rubber O ring makes a satisfactory seal.

The outer sleeve 13 is threaded 14 on the outside circumference of its upper portion. This outer sleeve 13 is attached to the upper wall 7 by studs 15 or otherwise connecting a lip 23, which projects from and encircles the outer sleeve 13, to the upper wall 7. The threads 14 of the outer sleeve 13 are engaged with the interior threads of the outer ring 16, which is attached to the adjustment ring 17 by studs 24. The lip 18, which projects from and encircles the top of the inner tube 11, is nested between an inwardly projecting lip 19 on the top of the adjustment ring 17 and the top edge of the outer ring 16. As the adjustment ring 17 and outer ring 16 turn as a single unit, the inner tube 11 is vertically adjusted by turning the adjustment ring 17. The inner tube 11 is prevented from turning with the adjustment ring 17 by a stud 20 or pin projecting through the outer sleeve 13 into a vertical slot 21 in the sidewall of the inner tube 11. This slot 21 is of sufficient height to permit the desired height adjustment of the tube. Thus, the height of the slot 8 can be adjusted without turning the slot, which permits maintaining the slot in a radial position with the collecting plate 9 at all heights.

Referring to FIG. 2, a gap or height indicator 59 may be included to permit the operator to determine the proper height of the slit 8 above the medium 68 in the collecting plate 9. A bracket 64 is fixedly attached to a side wall of the slit tube 11 by screws 67 or otherwise. An extension 66 of this bracket 64 extends to the end of the height indicator 59. The height indicator 59 is pivotably attached by a pin 65 to bracket 64. An adjustable arm 63 supporting a contact disc 62 is attached to this pivoting height indicator 59. Prior to commencing operation, the adjustable arm 63 is adjusted so that the bottom of the contact disc 62 is in the proper height in relation to the slit 8. The slit tube 11 is then lowered toward the medium 68 until the indicator 59 which pivots about the pin 65 is centered in the opening 61 through which it projects on the end of the extension 66. The shaded areas 60 above and below this center can be included to assist in making this determination.

Figure 4:
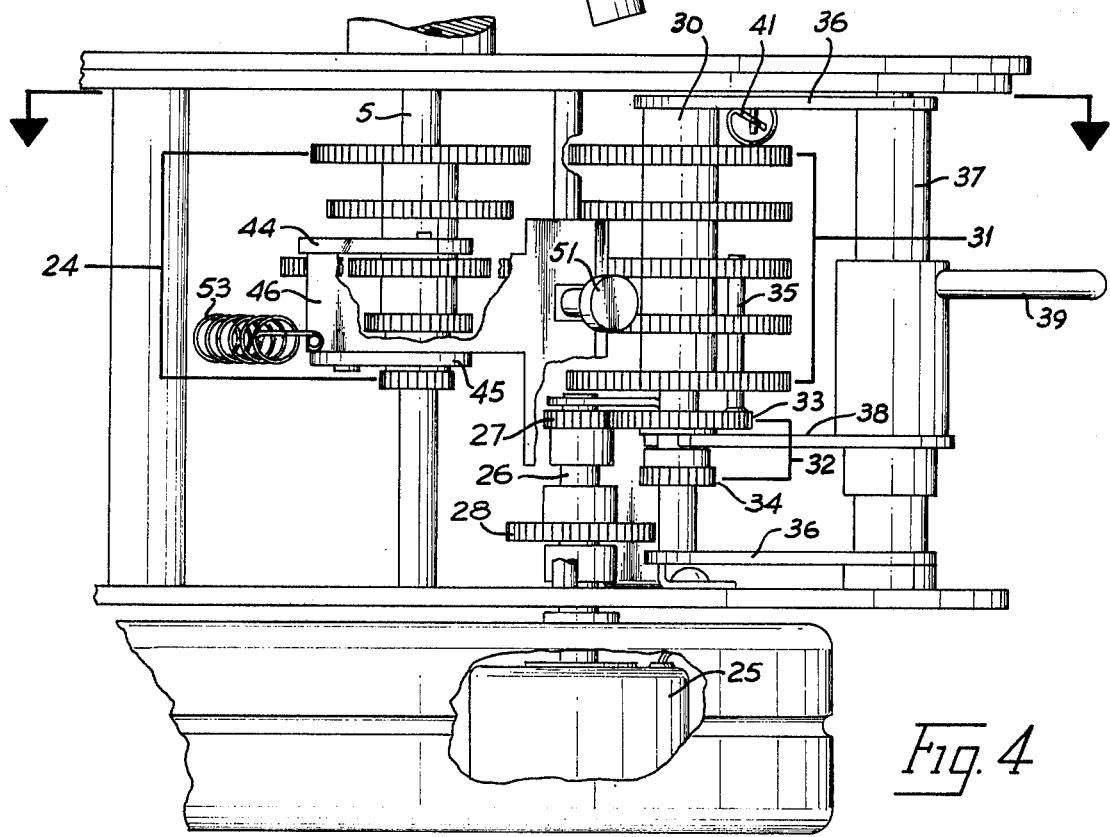
FIG. 4 is a front elevation of the lower base of the slit impact air sampler with the cover removed to illustrate the variable speed transmission therein.

As shown in FIG. 4, the rotating platform 4 is mounted on an output shaft 5, which is rotated by an electric or key wound motor 25 through a variable speed transmission. The motor 25 is directly connected to a drive shaft 26, which fixedly carries an upper co-axial gear 27 and lower co-axial gear 28 of a larger diameter. Parallel to the axis of rotation of the drive shaft 26 is the output shaft 5 which fixedly carries a stepped gear assembly 29, made up of a series of co-axial gears which are of progressively larger diameters from bottom to top. However, the stepped gear assembly 29 can have gears which are of progressively larger diameter from top to bottom.

The idler shaft 30 is parallel to the axis of rotation of output shaft 5 and located on the opposite side of the drive shaft 26 from the output shaft 5. The upper portion of the idler shaft 30 fixedly carries an upper gear assembly 31, made up of a series of co-axial gears of the same number as in the stepped gear assembly 29 and located in corresponding horizontal planes. Preferably, all of the gears in the upper gear assembly 31 are of the same diameter. The idler shaft 30 slidably carries on its lower portion a lower gear assembly 32, consisting of an upper co-axial gear 33 and lower co-axial gear 34 of a smaller diameter which are fixedly attached to each other. The upper gear 33 can be of a smaller diameter than the lower gear 34, provided that the upper gear 27 on the drive shaft 26 is of a larger diameter than the lower gear 28. The lower gear assembly 32 is slidably attached to the upper gear assembly 31 by a pin 35, which projects through a hole in one or more of the lower gears of the upper gear assembly 31. Thus, the lower gear assembly 32 is axially shiftable while at the same time rotating with the idler shaft 30. The lower gear assembly 32 can be slidably attached to the upper gear assembly 31 by slidably keying the lower gear assembly 32 to the lower part of the idler shaft 30. Thus, all of the gears on the idler shaft 30 rotate together. The idler shaft 30 is held in its vertical position by two support arms 36, which are rotatably carried on a support shaft 37 so that idler shaft 30 can be moved radially in relation to the axis of the support shaft 37. The lower gear assembly 32 is attached to a connecting arm 38, which is slidably and rotatably carried on the support shaft 37. A gear change lever 39 is fixedly attached to the connecting arm 38. This gear lever projects through a two position gate 40 on the cover of the lower base 2 as shown in FIG. 1.

Figure 5:
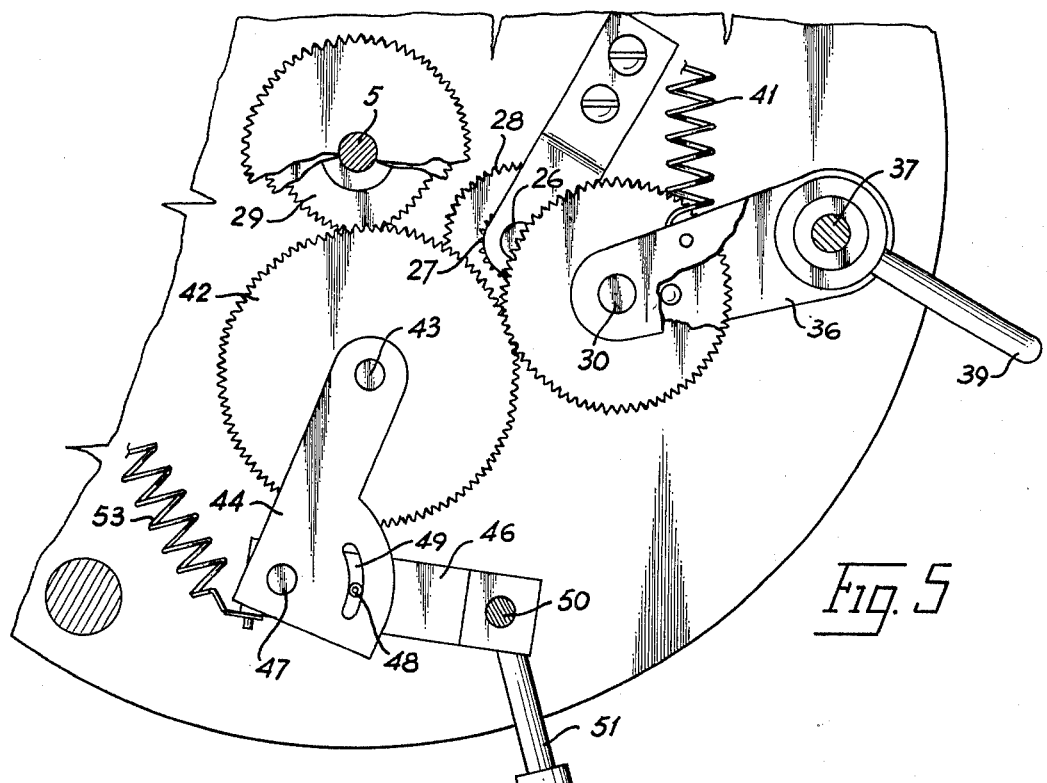
FIG. 5 is a view of the variable transmission as seen from above.

As shown in FIG. 4 and 5 the rotation speed of the idler shaft 30 can be changed by moving the gear change lever 39 to the right, which moves the idler shaft 30 radially around the support shaft 37 and away from the drive shaft 26. The gear change lever 39 can then be moved up or down and to the left into the desired gate position A or B 40 as shown in FIG. 1, which moves the idler shaft 30 radially towards the drive shaft 26. When the gear change lever is in gate position A, the upper gear 33 on the idler shaft 30 is enmeshed with the upper gear 27 on the drive shaft 26. When the gear change lever is positioned in gate B, the lower gear 34 on the idler shaft 30 is enmeshed with the lower gear 28 on the drive shaft 26. The gear on the idler shaft 30 is enmeshed with the corresponding gear on the drive shaft 26 and urged into the enmeshed position by a spring 41 attached to the support arm 36 and a suitable point on the lower base 2 as shown in FIG. 5.

As shown in FIG. 5, power is transmitted from the idler shaft 30 to the output shaft 5 through a transfer gear 42 which is enmeshed with a gear on the idler shaft 30 and the gear on the output shaft 5, located in the same horizontal plane. The transfer gear 42 is axially carried on short vertical shaft 43 which is axially parallel to the output shaft 5. This shaft 43 is supported between a horizontal upper support arm 44 and a corresponding parallel lower support arm 45 as shown in FIG. 4. As shown in FIG. 5, the upper support arm 44 is pivotally attached to the top of the support shoulder 46 by a pin 47. The lower support arm 45 is likewise pivotally attached to the bottom of the support shoulder 46. A pin 48 projects from the top of the support shoulder 46 into a slot 49 on the upper support arm 44 to limit the radial movement of the support arms 44 and 45 in relation to the support shoulder 46 so that the transfer gear 42 can be enmeshed with the appropriate gears on the output shaft 25 and idler shaft 30. The support shoulder 46 is pivotally and slidably attached to a support shaft 50. A gear change lever 51 is fixedly attached to the support shoulder 46 and projects through a gate 52 on the outer cover of the lower base 1 as shown in FIG. 1.

The speed of the rotating platform 4 can be changed by moving the gear change lever 51 to the right which disengages the transfer gear 42 and then moving the gear change lever up or down as desired in the vertical portion of the gate and then to the left into the desired gate position which engages the transfer gear 42 with the corresponding gears on the output shaft 5 and idler shaft 30 as shown in FIG. 5. A spring 53 attached to the support shoulder 46 and an appropriate place on the lower base enmeshes the transfer gear 42 and urges it in the enmeshed position except when the gear change lever 51 is moved as shown in FIG. 5. The motor 25 preferably turns the drive shaft 26 counterclockwise so that the gears on the idler shaft 30 are turning clockwise and the gears on the output shaft 5 are turning counterclockwise to facilitate the gears staying engaged during running without the use of a very strong spring 53.

The idler shaft 30 carries five gears 31 and the output shaft also carries five gears located in corresponding horizontal planes. The gate 52 has five corresponding positions. If more rotation speeds are desired, additional gears can be added to the output shaft 5 and the idler shaft 30. The number of gears on each of these shafts can also be reduced, but obviously at least two gears would be needed on each shaft for this gear change lever 51 to change the speed of rotation.

The combination of gear change levers 39 and 51 results in a total of ten rotation speeds. The left hand column of numbers 54, as shown in FIG. 1, represents the rotation speed of the rotation platform 4 in each corresponding gate 52 when gear change lever 39 is in the A position in the gate 40 with a given set of gears. The right column of numbers 55 represents the rotation speeds when the gear change lever 39 is in the B position in the gate 40.

The availability of ten rotation speeds for the rotation platform 4 permits the operator to adjust the speed to precisely the conditions encountered. The ability to adjust the height of the slit 8 above the rotation platform 4 without changing its radial alignment permits the operator to precisely adjust to the conditions encountered.

Obviously many modifications and variations of the present invention are possible in light of the above teachings. For example, a standard slit tube could be used with the variable speed transmission of this invention. The slit tube on this invention could also be used with a standard slit impact air sampler. It is, therefore, to be understood that within the scope of the invention may be individual modifications and variations other than as specifically described.

The embodiments of the invention in which an exclusive property or privilege is claimed are defined as follows:

1. An impact air sampler comprising the combination of:
   a. An impact chamber with an outlet passage;
   b. A rotating platform positioned in said impact chamber and mounted on an output shaft;
   c. An inlet slit tube projecting through a wall of said impact chamber with the slit located above said rotating platform, with means for the flow of air into said inlet slit and out of said outlet passage;
   d. A variable speed transmission for rotating said platform at variable speeds, said transmission having a drive shaft positioned parallel to the axis of rotation of said output shaft, said drive shaft fixedly carrying two co-axial gears of varying diameters, with means to rotate said drive shaft, said transmission having an idler shaft positioned parallel to the axis of rotation of said output shaft and located on the opposite side of said drive shaft from said output shaft, said idler shaft fixedly carrying a series of co-axial gears, said idler shaft also carrying two co-axial gears which are axially shiftable but rotate with the idler shaft, said gears being of approximately the same diameters as the gears on said drive shaft, means for selectively engaging a gear on the drive shaft with one of the axially shiftable gears on the idler shaft so that the larger gear on one of the shafts is engaged with the smaller gear on the other shaft so as to provide two rotation speeds for the idler shaft, said output shaft fixedly carrying a series of co-axial gears in varying diameters, with the transverse plane of each gear being located in the same place as the transverse plane of one of the fixedly attached gears on the idler shaft, said transmission having a transfer gear carried on a shaft axially parallel to the output shaft, means for moving said transfer gear from engagement with a gear on said output shaft and a gear in the same transverse plane on said idler shaft into a position clear of said gears and back into engagement with another gear on said output shaft and a gear in the same transverse plane on said idler shaft.

2. The impact air sampler of claim 1 wherein said inlet slit tube (c) can be vertically adjusted, projecting said tube through the upper wall so that the axis of the slit tube is located approximately midway between the center and periphery of said rotating platform, said slit tube comprising the combination of:
   a. an inner tube with a slit plate attached to the bottom of said inner tube;
   b. an outer sleeve fitted around the inner tube with means to prevent the inner tube from being rotated while permitting it to be vertically adjusted, said outer sleeve being threaded on the outside circumference of its upper portion, said outer sleeve being attached to the upper wall by attachment means;
   c. an outer ring fitted around said outer sleeve with interior threads engaged with the exterior threads of said outer sleeve, means for connecting said outer ring to said inner tube so said tube is vertically adjusted as said outer ring is rotated.

3. The impact air sampler of claim 2 wherein a height gauge is attached to said inlet slit tube (c) to measure the height of the slit above any medium located on the rotating platform.

4. The impact air sampler of claim 1 wherein in (d) the means to rotate said drive shaft is a key-wound motor, the two co-axial gears on the idler shaft are positioned on the lower portion of said shaft, the means for selectively engaging a gear on the drive shaft with one of the two co-axial gears on the idler shaft comprises the idler shaft being supported by at least one supporting member which is rotatably carried on a support shaft parallel to the idler shaft so that the idler shaft can be moved radially in relation to the axis of the support shaft, and a connecting arm attached to the two co-axial gears on the idler shaft and which is slidably and rotatably carried on the support shaft and means for moving said idler shaft radially and two co-axial gears slidably, wherein the means for moving said transfer gear from engagement comprises at least one supporting arm which is pivotably attached to a support shoulder which is pivotably and slidably attached to a transfer gear support shaft which is parallel to the axis of said drive shaft and means for moving said supporting arm and supporting shoulder radially and slidably about said transfer gear support shaft.

5. The impact air sampler of claim 2 wherein in (d) the means to rotate said drive shaft is a key-wound motor, the two co-axial gears on the idler shaft are positioned on the lower portion of said shaft, the means for selectively engaging a gear on the drive shaft with one of the two co-axial gears on the idler shaft comprises the idler shaft being supported by at least one supporting member which is rotatably carried on a support shaft parallel to the idler shaft so that the idler shaft can be moved radially in relation to the axis of the support shaft, and a connecting arm attached to the two co-axial gears on the idler shaft and which is slidably and rotatably carried on the support shaft and means for moving said idler shaft radially and two co-axial gears slidably, wherein the means for moving said transfer gear from engagement comprises at least one supporting arm which is pivotably attached to a support shoulder which is pivotably and slidably attached to a transfer gear support shaft which is parallel to the axis of said drive shaft and means for moving said supporting arm and supporting shoulder radially and slidably about said transfer gear support shaft.

6. The impact air sampler of claim 1 wherein the means to prevent the inner tube from being rotated comprises a slot in the side wall of said inner tube into which a pin attached to the outer sleeve projects, and the outer ring is connected to the inner tube by an outwardly projection lip encircling the top of the inner tube which is nested between the top edge of the outer ring and an inwardly projecting lip on the top of an adjustment ring which is attached to the outer ring.

7. The impact air sampler of claim 2 wherein the means to prevent the inner tube from being rotated comprises a slot in the side wall of said inner tube into which a pin attached to the outer sleeve projects and the outer ring is connected to the inner tube by an outwardly projection lip encircling the top of the inner tube which is nested between the top edge of the outer ring and an inwardly projecting lip on the top of an adjustment ring which is attached to the outer ring.

* * * * *